US006645507B2

(12) United States Patent
Bettle et al.

(10) Patent No.: US 6,645,507 B2
(45) Date of Patent: *Nov. 11, 2003

(54) SKIN PRODUCT HAVING CONTINUING ANTIMICROBIAL, ANTIVIRAL, ANTISEPTIC, AND HEALING PROPERTIES

(75) Inventors: Griscom Bettle, Sarasota, FL (US); William S. Coury, Sarasota, FL (US); Berno I. Pettersson, Perry, GA (US)

(73) Assignee: American Medical Research, Inc., Sarasota, FL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/331,817

(22) PCT Filed: Dec. 31, 1997

(86) PCT No.: PCT/US97/24220
§ 371 (c)(1),
(2), (4) Date: Jun. 25, 1999

(87) PCT Pub. No.: WO98/29085
PCT Pub. Date: Jul. 9, 1998

(65) Prior Publication Data
US 2003/0044435 A1 Mar. 6, 2003

Related U.S. Application Data
(60) Provisional application No. 60/033,796, filed on Dec. 31, 1996.

(51) Int. Cl.[7] .............................. A61K 6/00; A61K 7/00; A61K 7/075; A61K 7/09
(52) U.S. Cl. ................ 424/401; 424/70.19; 424/70.28; 424/70.31; 514/844; 514/937
(58) Field of Search ............................. 424/401, 70.19, 424/70.28, 70.31; 514/844, 937

(56) References Cited

U.S. PATENT DOCUMENTS

| 3,215,603 A | 11/1965 | Gross et al. |
| 3,716,633 A | 2/1973 | Viout et al. |
| 4,027,008 A | 5/1977 | Sokol |
| 4,228,259 A | 10/1980 | Kalopissis et al. |
| 4,381,919 A | * 5/1983 | Jacquet et al. .................. 8/405 |
| 4,567,203 A | 1/1986 | Bonadeo ...................... 514/844 |
| 4,976,953 A | * 12/1990 | Orr et al. ...................... 424/47 |
| 4,996,059 A | 2/1991 | Grollier et al. |
| 5,198,584 A | 3/1993 | Chan et al. |
| 5,358,667 A | 10/1994 | Bergmann |
| 5,804,167 A | 9/1998 | Schönrock et al. ........... 424/59 |
| 5,942,216 A | 8/1999 | Herb et al. |
| 5,948,416 A | 9/1999 | Wagner et al. .............. 424/401 |

FOREIGN PATENT DOCUMENTS

| CH | 680565 | 3/1990 |
| DE | 43 44 697 A | 6/1995 |
| EP | 0058853 A2 * | 9/1982 |
| EP | 0 146 350 A2 | 12/1983 |
| EP | 0 336 901 | 10/1989 |
| EP | 0 514 934 A1 | 11/1992 |
| FR | 1 517 743 | 8/1996 |
| GB | 2173515 A | 10/1986 |
| WO | WO 94/13257 | 6/1994 |
| WO | WO 96/32089 | 10/1996 |
| WO | WO 97/01326 | 1/1997 |

OTHER PUBLICATIONS

Derwent Abstract of JP 53127838 A (KANE); Nov. 1978.
Derwent Abstract of SU 1248604 A (KDSU–R) Aug. 1986.
Derwent Abstract of JP 63179812 A (SHIS) Jul. 1988.

* cited by examiner

Primary Examiner—Theodore J. Criares
(74) Attorney, Agent, or Firm—Needle & Rosenberg, P.C.

(57) ABSTRACT

A composition capable of forming a film that ionically bonds to the skin comprising: one or more active agents; a nonionic or substantially nonionic first film forming component; one or more cationic surfactants comprising one or more fatty moieties that are soluble in the first film forming component; and a liquid carrier. Also provided are stable emulsions of such compositions, compositions that are especially adapted to delivering medicinal agents to the surface of the skin, and methods for preparing such compositions.

20 Claims, No Drawings

SKIN PRODUCT HAVING CONTINUING ANTIMICROBIAL, ANTIVIRAL, ANTISEPTIC, AND HEALING PROPERTIES

RELATED APPLICATIONS

This application claims priority to U.S. Provisional Patent Application No. 60/033,796, filed Dec. 31, 1996.

BACKGROUND OF THE INVENTION

FIELD OF THE INVENTION

This invention relates generally to skin products, and particularly to emulsion-based skin products that can be applied to the skin to provide continuing antimicrobial, antiviral, antiseptic, and healing properties.

People often use soaps and bactericides to remove and exterminate undesirable contaminants such as dirt and bacteria from the skin, especially the hands. These products are typically applied to the skin while washing the hands under running water. The products have a limited temporal effect, however, because they are washed from the skin along with the dirt and bacteria during the washing process. Conventional soaps and bactericides do not, therefore, provide any lasting effect after they have been used. However, in many occupations, such as the medical profession, it is important to minimize and destroy harmful bacteria and viruses immediately when they contact the skin. A skin product that provided continued protection against contaminants with which the skin comes into contact, after being applied to the skin, would therefore be highly desirable. Such a product could also be adapted to deliver active agents, such as drugs, continuously to the skin.

SUMMARY OF THE INVENTION

In accordance with the purpose(s) of this invention, as embodied and broadly described herein, this invention, in one aspect, relates to a composition capable of forming a film that ionically bonds to the skin comprising: one or more active agents; a nonionic or substantially nonionic first film forming component; one or more cationic surfactants comprising one or more fatty moieties that are soluble in the first film forming component; and a liquid carrier.

The invention further provides a phase stable emulsion comprising: one or more quaternary ammonium compounds; one or more nonionic surfactants; one or more fatty esters; one or more fatty alcohols; and optionally one or more highly polar compounds; wherein the ratio of the sum of the moles of quaternary ammonium compounds, surfactants, and highly polar compounds, to the sum of the moles of fatty esters and alcohols is from about 0.8 to about 1.2.

The invention also provides an emulsion composition for delivering one or more active agents to the surface of the skin comprising a fatty phase and wherein the fatty phase comprises fatty acids, glycerides, and optionally other fatty components, at a molar ratio of fatty acids to glycerides and other fatty components from about 0.5 to about 3.5.

In another aspect the invention provides a process for preparing a phase stable emulsion comprising: forming an aqueous phase; forming a second phase comprising one or more fatty acids, and one or more fatty alcohols and/or one or more fatty esters; mixing the first and second phases to form an emulsion; and mixing an organic base with the emulsion; wherein: (a) the emulsion optionally comprises one or more quaternary ammonium compounds and/or highly polar compounds; and (b) the ratio of the sum of the moles of quaternary ammonium compounds, surfactants, and highly polar compounds, to the sum of the moles of fatty esters and fatty alcohols, is from about 0.8 to about 1.2.

In yet another aspect the invention provides a process for preparing a phase stable emulsion comprising: forming an aqueous phase; forming a second phase comprising one or more fatty acids, and one or more fatty alcohols and/or one or more fatty esters; mixing the first and second phases to form an emulsion at a temperature of from about 57 C. to about 80 C.; and mixing an organic base with the emulsion at a temperature of from about 57 C. to about 80 C.

Additional aspects and advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION OF THE PREFERRED EMBODIMENTS

The present invention may be understood more readily by reference to the following detailed description of preferred embodiments of the invention and the Examples included therein.

Before the present compounds, compositions and methods are disclosed and described, it is to be understood that this invention is not limited to specific synthetic methods, or to specific formulations or administration regimens, as such may, of course, vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "a fatty ester" includes mixtures of fatty esters, reference to "a liquid carrier" includes mixtures of two or more such carriers, and the like.

Ranges are often expressed herein as from about one particular value, and/or to about another particular value. When such a range is expressed, it is to be understood that a more preferred range is typically from the one particular value and/or to the other particular value. Similarly, when values are expressed as approximations, by use of the antecedent "about," it will be understood that the particular value is typically more preferred. It will further be understood that the endpoints of each of the ranges are significant both in relation to the other endpoint, and independently of the other endpoint.

In this specification and in the claims which follow, reference will be made to a number of terms which shall be defined to have the following meanings:

References in the specification and concluding claims to parts by weight, of a particular element or component in a composition or article, denotes the weight relationship between the element or component and any other elements or components in the composition or article for which a part by weight is expressed. Thus, in a composition containing 2 parts by weight of component X and 5 parts by weight component Y, X and Y are present at a weight ratio of 2:5, and are present in such ratio regardless of whether additional components are contained in the composition.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a residue of NaCl in solution, under appropriate conditions, refers to the sodium anion and chloride cation in solution.

The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like. The term "lower alkyl" intends an alkyl group of from one to six carbon atoms, preferably from one to four carbon atoms. The term "cycloalkyl" intends a cyclic alkyl group of from three to eight, preferably five or six carbon atoms.

"Optional" or "optionally" means that the subsequently described event or circumstance may or may not occur, and that the description includes instances where said event or circumstance occurs and instances where it does not. For example, the phrase "optionally substituted alkyl" means that the alkyl group may or may not be substituted and that the description includes both unsubstituted alkyl and alkyl where there is substitution.

By the term "effective amount" of a compound or property as provided herein is meant such amount as is capable of performing the function of the compound or property for which an effective amount is expressed. As will be pointed out below, the exact amount required will vary from process to process, depending on recognized variables such as the compounds employed and the processing conditions observed. Thus, it is not possible to specify an exact "effective amount." However, an appropriate effective amount may be determined by one of ordinary skill in the art using only routine experimentation.

The term "polymer" includes copolymers. Similarly, when names of polymers are expressed, copolymers that maintain the essential function of the polymer are also intended.

In one embodiment the invention is a creme or lotion composition that can be applied to the skin in order to: (1) cleanse and disinfect the skin; (2) impart continuing antimicrobial and antiviral properties to the surface of the skin; and (3) provide a hydrophobic protective and healing film next to the skin. Such a composition is preferably applied to the skin after the skin has been washed in order to lengthen the effectiveness of the composition. In another embodiment the composition is a creme or lotion that is applied to the skin in order to deliver a medicinally active agent to the surface of the skin.

In one aspect the composition is capable of forming a film that ionically bonds to the skin comprising: one or more active agents; a nonionic or substantially nonionic first film forming component; one or more cationic surfactants comprising one or more fatty moieties that are soluble in the first film forming component; and a liquid carrier. From about 20 to about 40 parts by weight of one or more active agents are typically present in the composition, although from about 25 to about 35 parts by weight are preferred. The ingredients that make up the first film forming component typically comprise from about 1 to about 5 parts by weight of the total composition, and preferably comprise from about 2 to about 4 parts by weight. The composition typically comprises from about 0.2 to about 5 parts by weight of cationic surfactant, and preferably comprises from about 1 to about 3 parts by weight cationic surfactant. From about 60 to about 80 parts by weight of the liquid carrier are typically present in the composition, although from about 65 to about 75 parts by weight are especially preferred.

The first film forming component is preferably insoluble in the liquid carrier, and present in the composition as an emulsion. When applied to the skin, the first film forming component forms a hydrophobic film that covers the skin as the liquid carrier evaporates. The hydrophobic film can serve several functions. The hydrophobic film can protect skin that may have become exposed by the scouring action of cleansers in the composition. The film can provide a suitable environment for the freshly-exposed skin to heal from the aggressive cleansing process. By bonding to the skin, the film can also exclude water and water soluble cleansing agents from the surface of the skin, and thereby prevent the cleanser from continuing to negatively scour the surface of the skin.

The hydrophobic film may also act as a foundation for imparting continuing properties to the skin. Antiviral and antibacterial agents can be incorporated into the film, and thereby provide residual protection against contaminants with which the skin may come into contact. The hydrophobic film may also act as a medium through which medicinal agents can migrate and be delivered to the skin.

The hydrophobicity of the film can, of course, vary. However, the film is preferably sufficiently hydrophobic, and the film forming component sufficiently insoluble, to exclude water (and dissolved active ingredients such as cleansers and bactericides) from the surface of the skin as a film is formed on the surface of the skin. The film that is formed is preferably sufficiently impervious to water to minimize the incidence of water (which can carry aggravating cleansers, bacteria and other undesirable constituents) migrating through the film barrier.

Numerous formulations can be used as the first film forming component. For example, the first film forming component can include natural and synthetic polymers and waxes. For reasons that will become apparent, preferred formulations solubilize fatty moieties, and can selectively incorporate fatty moieties from ionic compounds within their structure, while excluding other ionic moieties from the compound, upon drying to form a film. Waxes, which contain the esters of fatty acids and fatty alcohols (other than glycerol), are especially suitable ingredients for the first film forming component. Waxes that suitably interact with propolis to impart the desired properties to the film are especially preferred.

An especially suitable formulation for the first film forming component comprises natural or synthetic bees wax; propolis; one or more fatty acids; and one or more fatty alcohols. The fatty acids typically comprise from about 10 to about 26 carbon atoms, and the fatty alcohols typically comprise from about 10 to about 26 carbon atoms. In a preferred embodiment the fatty acid comprises from about 12 to about 18 carbon atoms, and the fatty alcohol comprises from about 12 to about 16 carbon atoms. In an even more preferred embodiment, the fatty acid comprises stearic acid, and the fatty alcohol comprises cetyl alcohol or myristic alcohol. In addition to being an integral element of the film, the fatty acid also preferably acts as a surfactant after it has been neutralized. The fatty alcohol preferably acts as an emulsifying agent. The alcohol can be substituted with groups such as amides, alkyl, and allyl groups, to tailor the alcohol to a specific set of requirements.

The bees wax is preferably natural, with crude, filtered bees wax being especially preferred. The bees wax can, however, be synthetic, or substituted with other natural waxes, as long as the wax possesses a net positive charge and a chemical similarity to natural bees wax, and interacts favorably with propolis. A particularly suitable synthetic bees wax is the synthetic wax manufactured by Alzo, Inc. of Sayreville, N.J., under the trade name Waxenol-8-22 (arachidyl behenate).

The propolis may preferably comprise propolis wax or propolis resin. The propolis may constitute a distinct ingredient of the composition, or it may be added as part of another ingredient such as the bees wax. The weight ratio of propolis to bees wax preferably meets or exceeds the ratio at which propolis and bees wax naturally occur (about 26:74).

The first filming component may optionally further comprise the solution residue of a monoester monoglyceride. The acidic residue of the monoester monoglyceride preferably comprises from about 10 to about 18 carbon atoms, and most preferably comprises 12 carbon atoms. The monoglyceride may be unsaturated, and may have up to three double bonds. Saturated monoglycerides are, however, especially preferred. The monoglyceride may also be substituted with, for example, one or more alkyl groups, especially the lower alkyl groups. A particularly suitable monoglyceride is lauricidin.

The first film forming component typically comprises from about 1 to about 12 parts by weight monoester glyceride, from about 0.2 to about 3.0 parts by weight bees wax, from about 0.1 to about 1.5 parts by weight propolis, from about 1.5 to about 10 parts by weight of one or more fatty acids, and from about 1 to about 8 parts by weight one or more fatty alcohols, independently or in combination. The first film forming component preferably comprises from about 2 to about 6 parts by weight monoester glyceride, from about 0.5 to about 1.5 parts by weight bees wax, from about 0.2 to about 0.6 parts by weight propolis, from about 3 to about 5 parts by weight of one or more fatty acids, and from about 2 to about 4 parts by weight of one or more fatty alcohols, independently or in combination.

The composition also preferably comprises a cationic surfactant, preferably comprising one or more fatty moieties. It is believed that the cationic surfactant binds ionically to the anionic sites on the surface of the skin, and, because the fatty moieties from the cationic surfactant are solubilized in the first film, anchors the film to the skin. It is also believed that the surfactant, by drawing the film toward the skin, helps to exclude water from the surface of the skin. The surfactant is preferably sufficiently cationic to achieve this anchoring function. Similarly, the fatty moieties preferably are sufficiently soluble and large, and have sufficient interaction with the film, to achieve this anchoring function. For example, fatty moieties comprising from about 12 to about 22 carbon atoms, and especially fatty moieties comprising about 18 carbon atoms, are most preferred.

The cationic surfactant preferably makes up at least 0.20 wt. % of the composition, and preferably comprises no more than about 5.0 wt. % of the composition. Less cationic surfactant than 0.20 wt. % is not evenly distributed across the surface of the film, and therefore is not as effective to evenly bond the film to the skin, and uniformly exclude water from the surface of the skin.

In one embodiment the fatty cationic surfactant of the composition comprises an ammonium compound that is substituted with at least one lower alkyl moiety. In another embodiment the ammonium compound is substituted with from one to three lower alkyl moieties, and one or more fatty moieties comprising from about 8 to about 22 carbon atoms, preferably from about 16 to about 22 carbon atoms. The fatty moiety can preferably be aryl, aliphatic, cycloaliphatic, saturated or unsaturated, straight or branched. In a more particular embodiment the cationic surfactant comprises the solution residue of dimethyl distearate ammonium chloride. A dimethyl, ditallow ammonium chloride residue, with its broader molecular weight distribution, is also preferred.

The liquid carrier for the composition can also vary. Indeed, any carrier that does not substantially interfere with the components or the function of the components, and which allows a film to form and thereby exclude the carrier from the skin surface as it evaporates, is suitable. Exemplary carriers include water, and lower molecular weight alcohols such as ethanol, isopropyl alcohol, and propylene glycol, although water is generally preferred for the particular ingredients described in this document.

The composition may comprise one or more active agents, which are chosen based upon the properties that one desires from the composition. For example, in one embodiment the composition may include an aggressive cleansing or skin preparation ingredient. Such active agents cleanse the surface of the skin immediately upon application of the composition to the skin, and cleanse the skin sufficiently before a film is formed from the first film forming component, and before the first film forming component excludes the active agents from the surface of the skin.

Cleansing ingredients may be capable of removing microbials, viruses, and other foreign contaminants from the surface of the skin. Cleansing ingredients may also be capable of scouring dead and dying layers of skin from the skin surface. The cleansing ingredient may suitably comprise non-ionic surfactants because: (1) this class of compounds readily cleanses the skin and removes the fatty dead and dying layers on the outer surface of the skin; (2) this class of compounds is typically very soluble in the water base of the composition; (3) this type of compound is an effective antiviral compound; and (4) this class of compounds allows the proper functioning of the other active ingredients of the composition.

Surfactants are particularly suitable because of their ability to cleanse at the interface of the liquid composition and the outer layers of the skin. A particularly suitable nonionic surfactant is sold under the trade mark Triton X-100, and comprises octoxynol, most suitably having 9–10 repeating units of ethoxylation. Another particularly suitable nonionic surfactant is nonoxynol-9, which can be used alone or in combination with other surfactants.

Suitable antimicrobial and cleaning active agents that can be incorporated into the composition include propylene glycol, berberine sulfate, various quaternary ammonium compounds, dimethyl benzethonium chloride, parachlorometaxylanol, nonoxynol-9, chlorohexadine gluconate, and lauricidin (glycerol monolaurate). Other active agents include skin healing emollient ingredients such as allantoin and dimethicone, fragrances and antioxidants.

It is also possible to include active agents with medicinal properties in the composition which, when delivered to the surface of the skin, are absorbed through the skin and metabolized by the body. Any active agent that is fat soluble, or which can be rendered fat soluble, is a suitable candidate for delivery through the compositions of the present invention, because such agents are capable of migrating through the first film formed by the composition, and thereafter being absorbed by the skin.

When the composition is used to deliver medicinal active agents, the composition may preferably be modified by the addition of a suitable partitioning agent. Such partitioning agents preferably comprise from about 0.1 to about 3.0 wt. % of the composition, and even more preferably comprise from about 0.3 to about 1.5 wt. % of the composition. Partitioning agents can be incorporated in the composition in order to (1) facilitate the migration of active agents through the film, and (2) modulate the skin surface to facilitate penetration of the skin by the active agents. Suitable partitioning agents include carbomers, hydroxymethylcellulose, and glyceridyl monooleate, as taught, for example, by Ogiso et al., in J. Pharm. Sci. 84:482–488 (1995), by Roy et al., in Int'l Jnl of Pharm. 110:137–145 (1994), and by Niazy et al., in AAPS 9th Ann. Mtg. Abst. 7080. Pharm Res. 11:5194 (1994), the disclosure from the above references being hereby incorporated by reference.

A particularly effective class of partitioning agents for use with the compositions of the present invention are the nonionic polyethoxylated fatty ethers and alcohols. The molecular weight of these agents, and their limited solubility in the liquid carrier, cause them to form a layer on the surface of the skin even before the first film forming component forms a film. After the film has formed, it is believed that these agents interact with the cationic surfactants that are anchored to the film in a manner that facilitates the transmission of active agents from the film into the skin. Moreover, the ethoxylation of the compounds appears to minimize and prevent undue irritation of the skin by these surfactant compounds. The degree of ethoxylation also appears to affect the rate at which active agents are partitioned by the partitioning agent.

The effectiveness of the partitioning agent at facilitating the transmission of an active agent varies depending upon the size and polarity of the active agent. In general, the size of the active agent and the size of the partitioning agent are directly related, so that larger active agents require larger partitioning agents. The degree of ethoxylation of the partitioning agent is also directly related to the size of the active agent and the polarity of the active agent.

The degree of ethoxylation of the partitioning agent typically ranges from about 10 to about 400 units of ethoxylation, although it preferably ranges from about 10 to about 100 units of ethoxylation, and most preferably ranges from about 10 to about 20 units of ethoxylation. The size of the partitioning agent typically ranges from about 12 to about 36 carbon atoms, and preferably ranges from about 12 to about 18 carbon atoms. Particularly suitable partitioning agents include polyoxy(10)O-ethanol and ceto stearyl alcohol.

Glycerides, including mono-, di-, and triglycerides, and alkoxyglycerols and alkylglycerols, are particularly suitable as active agents, or as carriers for active agents, in such transdermal applications. These components have independent medicinal properties, are capable of independently migrating through the film, and can also solubilize other fat soluble active agents and carry them through the first film to the surface of the skin. Suitable glycerides include, lauricidin, vitamin D suspended in palm oil, conjugated linoleic acid ("CLA"), and gamma linolenic acid ("GLA"). Highly unsaturated oils are also especially suitable active agents in such transdermal applications because such oils have an antioxidant benefit when transported through the skin, and in addition they are effective transport vehicles for fat soluble active agents.

The composition may also comprise one or more anionic surfactants having one or more fatty moieties that are soluble in the first film forming component. The fatty acids that comprise the first film forming component are typically neutralized during preparation of the composition, and are especially suitable anionic surfactants. These surfactants are believed to be capable of forming a substantially discreet layer in the dried structure on the skin. Due to the unique structures of these anionic surfactants, they are capable of anchoring in the film through their fatty moieties, with their anionic portion being typically oriented on the opposite side of the film from the skin (because the anionic charge is repelled by the anionically charged skin surface). Because the anionic surfactant is located on the exposed side of the film, and is anchored in the film through its fatty moieties, the surfactant imparts continuing properties to the film. In a preferred embodiment the fatty moieties of the anionic surfactant comprise from about 12 to about 22 carbon atoms. A preferred anionic surfactant is a salt of stearic acid or sodium lauryl sulfate.

In another embodiment the composition comprises a nitrogenous organic base. The base stabilizes the emulsion when the composition comprises an emulsion, although how such stabilization is achieved is not well understood. The base is preferably triethanolamine, tromethamine, or a tris amino alcohol compound such as tris(hydroxymethyl) aminomethane, tris(hydroxymethyl)aminoethane, with triethanolamine and tromethamine being especially preferred. The nitrogenous base preferably forms an adduct with the fatty acid in the first film forming component. In a preferred embodiment the first film forming component is modified with a fatty acid/nitrogenous base adduct formed by mixing the fatty acid with one or more nitrogenous bases at temperatures between about 57 and about 80 C. Such adduct, in combination with the cationic surfactant, make at least one side of the first film essentially lipophilic and positively charged, and thereby attracted by the negatively charged skin.

Other ingredients may be included in the composition. Tetra sodium EDTA, for example, is preferably added to the composition in order to partially neutralize an emulsion of the composition. EDTA may also sequester any hard components of the water and further reduce the potential for any negative interactions between the hard components of the water and the active ingredients of the composition. From about 0 to about 0.5 parts by weight of EDTA are typically employed. A thickener can also be added to the composition in order to increase its viscosity, and obtain a creme product suitable for applying and rubbing into skin. Particularly suitable thickening agents include carboxypolymethylene (carbopol) and sodium carboxymethyl cellulose, present in the composition at from about 0 to about 0.4 parts by weight. Other ingredients that can be included in the composition include process aids such as glycerin and propylene glycol, emulsion stabilizers for the stearic acid such as cetyl alcohol, and preservatives such as chlorohexadine gluconate.

Additional ingredients can be added to the composition to build upon the layering effect of the composition, and to provide additional properties to the composition. In particular, in order to improve the residual antimicrobial and antiviral properties of the composition, an outer film-forming component can be added to the composition. The outer film-forming component can be comprised of ingredients that form a substantially discreet film after the hydrophobic first film has formed, and therefore which surrounds the hydrophobic film. If properly formulated, the outer film traps and encapsulates antimicrobial and antiviral components that may be contained in the composition. As the outer film becomes worn the antimicrobials are exposed gradually, thereby providing residual antimicrobial properties to the composition.

Although other film-forming ingredients will be apparent to workers skilled in the art, a particularly suitable outer film forming ingredient is polyvinyl pyrolidone (PVP), because it is initially soluble in water, but becomes insoluble upon drying and forming a film. It is believed that PVP, which can be added to the composition as a waxy non-soluble phase, coalesces and forms an outer film after the hydrophobic film has formed. It is believed that the outer film forms after the hydrophobic film has formed because the hydrophobic film forming ingredients respond more quickly to the evaporation of water from the composition and the resultant concentration of non-water ingredients in the composition. In essence, the hydrophobic film components are less soluble than the outer film ingredients and therefore precipitate first as water from the composition evaporates. Some of the active agents become entrapped between the hydrophobic film and the PVP outer film, it is further believed, because these active agents effectively precipitate from solution after the hydrophobic film has formed but before the outer film has coalesced. Because nonionic surfactants are the most soluble component of the composition, the outer film probably coalesces before the non-ionic surfactants precipitate from solution, and the outer film probably excludes and expels any non-ionic surfactants further from the skin, where they can provide desired residual effects.

It is believed that the composition of the invention forms one or more substantially discreet layers when applied to the skin. For example, the composition typically comprises a first hydrophobic film and a second outer film. Another layer can be present between these two layers that comprises active ingredients. For example, a layer of anionic moieties (from the fatty anionic surfactants) will typically coat the surface of the first hydrophobic film opposite the skin. Other active agents that precipitate from the composition before the second film forms can also form a layer between the first and outer films. Moreover, when the second film forms it can exclude other active agents that are still solubilized in the liquid carrier, and thereby form an additional layer on the outside of the outer film.

These layers will typically be substantially discreet. In many instances, however, various components of the composition will separate into different layers of the composition. This can happen, for example, if some of the ingredients that comprise the first film forming component are not incorporated in the film, or if some of the cationic surfactant doe not end up between the first film and the skin.

In some compositions the separation of ingredients among layers can be done by design. This is especially true of compositions used to deliver medicinal agents to the surface of the skin. In such compositions the medicinal agent will preferably be at least partially soluble in the first film. Some compositions may, however, comprise more medicinal agent in the composition than can be solubilized by the film, and as a result the medicinal agent may separate among the layers of the composition.

Thus, the first film that eventually forms from the first film forming component can incorporate in its structure various of the other ingredients contained in the composition. Active agents, in particular, are often incorporated into the film in order to enhance the effectiveness of the active agent.

The compositions of the invention preferably are about neutral, and even more preferably slightly basic. For example, compositions having a pH of from about 6.5 to about 7.5 are preferred. Compositions having a pH of from about 7.1 to about 7.5 are even more preferred.

In another aspect the invention provides a phase stable emulsion comprising one or more quaternary ammonium compounds; one or more nonionic surfactants; one or more fatty esters; one or more fatty alcohols; and optionally one or more highly polar compounds. In a particularly preferred embodiment the above components are present at a preferred ratio at the moment that the emulsion is formed. Components that are added to the composition after the emulsion has formed are not included in the ratio. The ratio of the sum of the moles of quaternary ammonium compounds, surfactants, and highly polar compounds to the sum of the moles of fatty esters and alcohols is preferably from about 0.8 to about 1.2. In an even more preferred embodiment the ratio is about 1.0.

Highly polar compounds that are included in the ratio include those compounds that are ionic and that have a dipole moment that exceeds the dipole moment of methanol. Highly polar compounds are typically added to increase the solubility of nonpolar compounds in polar solvents, although they can also be added as active agents. For example, polar compounds that contain sulfur are preferred when using the composition to treat burns because they are a source of sulfur which is used to heal damaged skin. Highly polar compounds include, for example, zinc sulfate, calcium propionate, and dimethyl sulfone (MSM).

In another aspect the invention provides a composition that is present in the form of an emulsion comprising a fatty phase, wherein the fatty phase comprises one or more fatty acids. The fatty phase further comprises one or more glycerides, typically mono-, di-, or tri-, but preferably triglycerides, alkoxyglycerols, and alkyl glycerols, such as are in natural shark oil, and optionally comprises one or more other fatty components such as fatty esters and fatty alcohols. In a preferred embodiment for delivering medicinal active agents to the surface of the skin, the molar ratio of the one or more fatty acids to the one or more glycerides and other fatty components is from about 1:2 to about 3.5:1, even more preferably from about 1:1 to about 2.5:1, and still even more preferably the ratio is about 2:1. It has been found that a composition having fatty acids and glycerides within this range of ratios are exceptional for transdermally delivering active agents, and that the ratio can be varied depending upon the transdermal effect desired for a particular system. Suitable glycerides typically comprise from about 10 to about 36 carbon atoms, can be conjugated or saturated, and are generally liquid at room temperature.

The invention also provides a process for preparing suitable compositions. In one aspect the invention provides a process for preparing a phase stable emulsion comprising: forming an aqueous phase; forming a second phase comprising one or more fatty acids, and one or more fatty alcohols and/or one or more fatty esters; mixing the first and second phases to form an emulsion; and mixing an organic base with the emulsion; wherein: (a) the emulsion optionally comprises one or more quaternary ammonium compounds, one or more surfactants, and/or highly polar compounds; and (b) the ratio of the sum of the moles of quaternary ammonium compounds, surfactants, and highly polar compounds, to the sum of the moles of fatty esters and fatty alcohols is from about 0.8 to about 1.2, preferably about 1.0. The emulsion is preferably formed at a temperature of from about 57 C. to about 80 C., preferably about 70 C. Moreover, the organic base is preferably mixed with the emulsion at a temperature of from about 57 C. to about 80 C., preferably about 70 C. The fatty ester(s) may optionally be added to the aqueous phase, although preferably they are included in the fatty phase.

The pH of the emulsion is preferably adjusted after the organic base is added to the emulsion to from about 7.1 to about 7.4. One or more active agents may be added to the aqueous phase, the second fatty phase, or the emulsion before or after it has been stabilized. In a particularly preferred embodiment some or all of the active agents are cationic In another embodiment the invention provides a process for preparing a phase stable emulsion comprising: forming an aqueous phase; forming a second phase comprising one or more fatty acids, one or more fatty alcohols, and one or more fatty esters; mixing the first and second phases to form an emulsion at a temperature of from about 57 C. to about 80 C.; and mixing an organic base with the emulsion at a temperature of from about 57 C. to about 80 C. In a particularly suitable embodiment the second phase comprises fatty acids at a molar ratio of fatty acids to glycerides and other fatty components of from about 1:2 to about 3.5:1, more preferably from about 1:1 to about 2.5:1, and most preferably about 2:1.

Where possible, only highly purified ingredients should be used. For example, the fatty esters should be triple distilled when possible. Similarly, with the naturally occurring ingredients, unwanted compounds such as heavy metals may be removed if done so without destroying the desired properties of the natural molecules. Other compounds can, of course, be substituted for the specific ingredients disclosed herein, as discussed in the preceding paragraphs and as understood by workers skilled in the art.

Experimental

The following examples are put forth so as to provide those of ordinary skill in the art with a complete disclosure and description of how the compounds claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at room temperature, and pressure is at or near atmospheric. Listed compounds are commercial grade.

EXAMPLE 1

An aqueous phase was first prepared by mixing the following components in the weight proportions listed. The aqueous phase was heated to 70 C. and mixed until creamy and uniform.

| NAME OF INGREDIENT | PARTS BY WEIGHT |
| --- | --- |
| D.I. water | 63.14 |
| Merquat 550 Polyquaternium-7 | 1.150 |
| Dimethyl Distearate Ammonium Chloride | 1.300 |
| Berberine Hydrochloride | 0.013 |
| Active Agents | 4.75 |

A fatty phase was next prepared by mixing the following components in the weight proportions listed, and heating the mixture to 70 C. 0.500 parts by weight lemon oil were then added to the mixture. The fatty phase thus formed was then added to the aqueous phase, and mixed until uniformly consistent. Temperature was maintained at 70 C.

| NAME OF INGREDIENT | PARTS BY WEIGHT |
| --- | --- |
| Stearic Acid | 3.750 |
| Cetyl Alcohol | 2.955 |
| Lauricidin | 3.150 |
| Propolis | 0.400 |
| Crude Bees Wax | 1.000 |
| Other Active Agents | 3.450 |

A third mixture was then prepared by combining the following ingredients at the weight proportions listed, at ambient temperature. The third mixture was then combined with the above mixture under high shear agitation to form an emulsion, with the temperature maintained at 70 C.

| NAME OF INGREDIENT | PARTS BY WEIGHT |
| --- | --- |
| D.I. Water | 3.000 |
| TEA | 1.540 |
| Tetra Na EDTA (solid) | 0.300 |

The emulsion was allowed to cool to 50 C., and 4.53 parts by weight of processing aids were mixed with the emulsion. 2.5 parts by weight of other active agents were then added to the emulsion, and the pH was lowered to about 7.4 with citric acid.

EXAMPLE 2

An emulsion was formed substantially following the procedure of Example 1. The aqueous phase contained:

| NAME OF INGREDIENT | PARTS BY WEIGHT |
| --- | --- |
| Water | 65.01 |
| Dimethyl Sulfone | 0.830 |
| Dimethyl Distearate Ammonium Chloride | 4.500 |
| Active Agents | 3.683 |

The fatty phase contained:

| NAME OF INGREDIENT | PARTS BY WEIGHT |
| --- | --- |
| Stearic Acid | 4.421 |
| Cetyl Alcohol | 4.119 |
| Crude Bees Wax | 0.900 |
| Propolis | 0.750 |
| Lauricidin | 3.840 |
| Glycerides | 3.993 |
| Cetyl Lactate | 0.250 |
| Ascorbyl Palmitate | 0.150 |
| Active Agents | 0.575 |

4.66 parts by weight of processing aids were added to the mixture. 2.319 parts by weight of triethanolamine were then added to the mixture to adjust the pH to 6.9.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A process for preparing a phase stable emulsion comprising:
   a. forming an aqueous phase comprising a quaternary ammonium compound as a cationic surfactant;
   b. forming a second phase comprising one or more fatty acids, and one or more fatty alcohols and/or one or more fatty esters;
   c. mixing the first and second phases to form an emulsion; and
   d. mixing a nitrogenous organic base with the emulsion to produce a salt of the one or more fatty acids and improve the stability of the emulsion;

wherein: (a) the emulsion optionally comprises one or more surfactants, and/or highly polar compounds; and (b) the ratio of the sum of the moles of quaternary ammonium compounds, surfactants, and highly polar compounds, to the sum of the moles of fatty esters and fatty alcohols is from about 0.8 to about 1.2, and (c) the emulsion has a pH from about 6.5 to about 7.5.

2. The process of claim 1 wherein the ratio is about 1.0.

3. The process of claim 1 wherein the emulsion is formed at a temperature of from about 57 C to about 80 C, and the organic base is mixed with the emulsion at a temperature of from about 57 C to about 80 C.

4. The process of claim 1 further comprising adjusting the pH of the emulsion after the addition of the organic base to from about 7.1 to about 7.4.

5. The process of claim 1 further comprising adding one or more active agents to the aqueous phase, the second phase, or the emulsion.

6. The process of claim 1 wherein mixing the nitrogenous organic base with the emulsion produces a phase stable emulsion.

7. The process of claim 1 wherein one or more active agents is added to the emulsion after the emulsion has been stabilized.

8. The process of claim 1 wherein the nitrogenous organic base forms an adduct with the fatty acid in combination with the cationic surfactant.

9. The process of claim 1 wherein the nitrogenous organic base reacts with the fatty acid to produce an anionic surfactant.

10. The process of claim 1 wherein the quaternary ammonium compound is substituted with from one to three lower alkyl moieties, and one or more fatty moieties comprising from about 8 to about 22 carbon atoms.

11. The process of claim 1 wherein the quaternary ammonium compound comprises a dimethyl distearate ammonium or a dimethyl ditallow ammonium cation.

12. The process of claim 1 wherein the nitrogenous organic base comprises triethanolamine, tromethamine, or tetrasodium EDTA.

13. The process of claim 1 wherein the organic base comprises a tris amino alcohol compound.

14. A composition produced by process of claim 1.

15. The composition of claim 14 comprising an adduct of the organic base with the fatty acid in combination with the cationic surfactant.

16. The composition of claim 1 that is capable of forming a film that binds ionically to the skin.

17. The composition of claim 14 comprising a glyceride.

18. The composition of claim 14 comprising a wax.

19. The composition of claim 14 comprising an antimicrobial agent.

20. The composition of claim 14 comprising a cleansing ingredient.

* * * * *

UNITED STATES PATENT AND TRADEMARK OFFICE
CERTIFICATE OF CORRECTION

PATENT NO.    : 6,645,507 B2
DATED         : November 11, 2003
INVENTOR(S)   : Coury et al.

It is certified that error appears in the above-identified patent and that said Letters Patent is hereby corrected as shown below:

<u>Column 14,</u>
Line 28, please delete the number "1" and substitute the following: -- 14 --

Signed and Sealed this

Eleventh Day of May, 2004

JON W. DUDAS
*Acting Director of the United States Patent and Trademark Office*